United States Patent
Zhang et al.

(10) Patent No.: US 11,733,405 B1
(45) Date of Patent: Aug. 22, 2023

(54) SYSTEM FOR TIMING PICKOFF OF QUALIFIED SIGNALS

(71) Applicant: Siemens Medical Solutions USA, Inc., Malvern, PA (US)

(72) Inventors: Nan Zhang, Knoxville, TN (US); Martin Judenhofer, Knoxville, TN (US); Joshua Kolb, Maryville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 17/663,056

(22) Filed: May 12, 2022

(51) Int. Cl.
*G01T 1/208* (2006.01)
*A61B 6/03* (2006.01)
*G01T 1/29* (2006.01)
*G01T 1/172* (2006.01)
*G01T 1/24* (2006.01)

(52) U.S. Cl.
CPC .............. *G01T 1/208* (2013.01); *A61B 6/037* (2013.01); *G01T 1/172* (2013.01); *G01T 1/248* (2013.01); *G01T 1/2985* (2013.01)

(58) Field of Classification Search
CPC ....... G01T 1/2985; G01T 1/208; G01T 1/248; G01T 1/172
See application file for complete search history.

(56) References Cited

U.S. PATENT DOCUMENTS

| | | | | |
|---|---|---|---|---|
| 5,097,147 A * | 3/1992 | Stuebing | ................ | H03K 5/153 327/78 |
| 5,608,221 A * | 3/1997 | Bertelsen | .............. | G01T 1/1642 250/363.04 |
| 2009/0236532 A1* | 9/2009 | Frach | .................... | G01T 1/1611 250/363.04 |
| 2013/0087710 A1* | 4/2013 | Zhang | ................... | G01T 1/1647 250/362 |

OTHER PUBLICATIONS

"Initial Measurements with the PETsys TOFPET2 ASIC Evaluation Kit and a Characterization of the ASIC TDC", IEEE TRPMS Special Issue PSMR2018—7th Conference on PET/MR and SPECT/MR, Aug. 15, 2018, DOI: 10.1109/TRPMS.2018.2884564, (pp. 1-11, 11 total pages).
ORTEC "Fast-Timing Discriminator Introduction", Advanced Measurement Technology, https://www.ortec-online.com/-/media/ametekortec/, Oct. 22, 2021, (pp. 1-9, 9 total pages).

* cited by examiner

*Primary Examiner* — David P Porta
*Assistant Examiner* — Casey Bryant

(57) ABSTRACT

Systems and methods include an analog-to-logic circuit and a digital processing component. The analog-to-logic circuit receives a first electrical signal, outputs a first logic signal indicating whether or not a voltage of the first pulse is greater than a first threshold voltage, and outputs a second logic signal indicating whether or not the voltage of the first pulse is greater than a second threshold voltage. The digital processing component receives the first logic pulse and the second logic pulse, determines, based on the second logic signal, if the first pulse is valid, and determines, based on the first logic signal, a first trigger time associated with the first pulse.

20 Claims, 7 Drawing Sheets

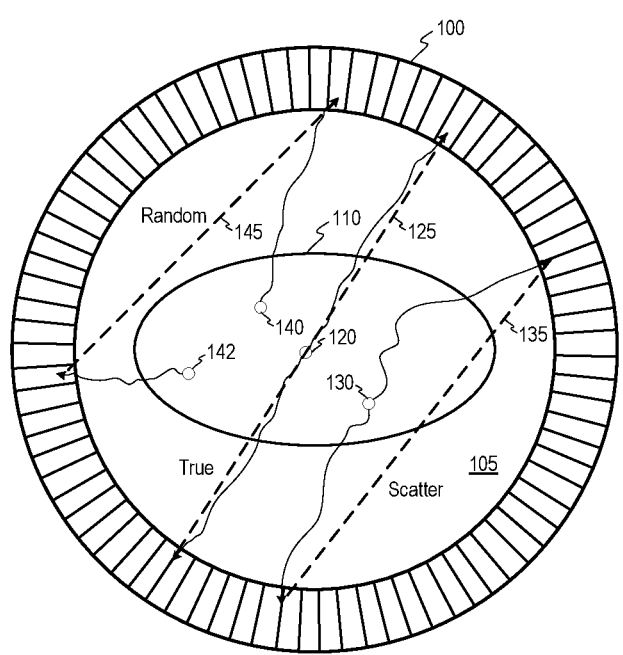 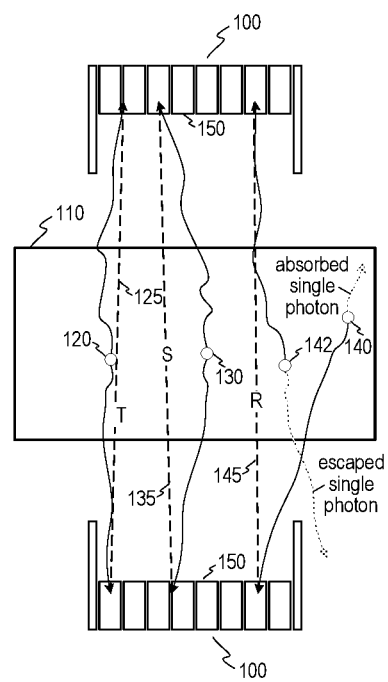
FIG. 1a  FIG. 1b

| DETECTOR d2390 | |
|---|---|
| $t_1$ | VALID? |
| 23 | |
| | |
| | |
| | |

FIG. 7a

| DETECTOR d2390 | |
|---|---|
| $t_1$ | VALID? |
| 23 | No |
| | |
| | |
| | |

FIG. 7b

| DETECTOR d2390 | |
|---|---|
| $t_1$ | VALID? |
| 23 | No |
| 39 | |
| | |
| | |

FIG. 7c

| DETECTOR d2390 | |
|---|---|
| $t_1$ | VALID? |
| 23 | No |
| 39 | No |
| | |
| | |

FIG. 7d

| DETECTOR d2390 | |
|---|---|
| $t_1$ | VALID? |
| 23 | No |
| 39 | No |
| 78 | |
| | |

FIG. 7e

| DETECTOR d2390 | |
|---|---|
| $t_1$ | VALID? |
| 23 | No |
| 39 | No |
| 78 | Yes |
| | |

FIG. 7f

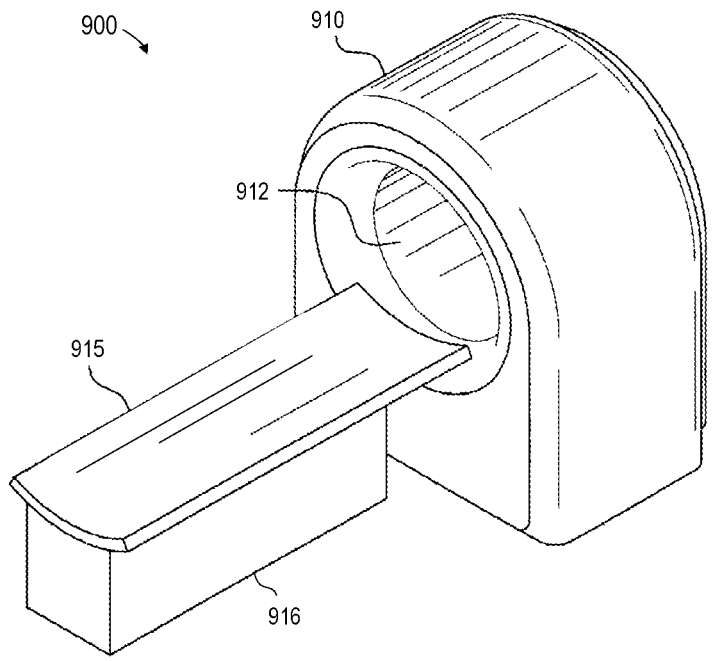
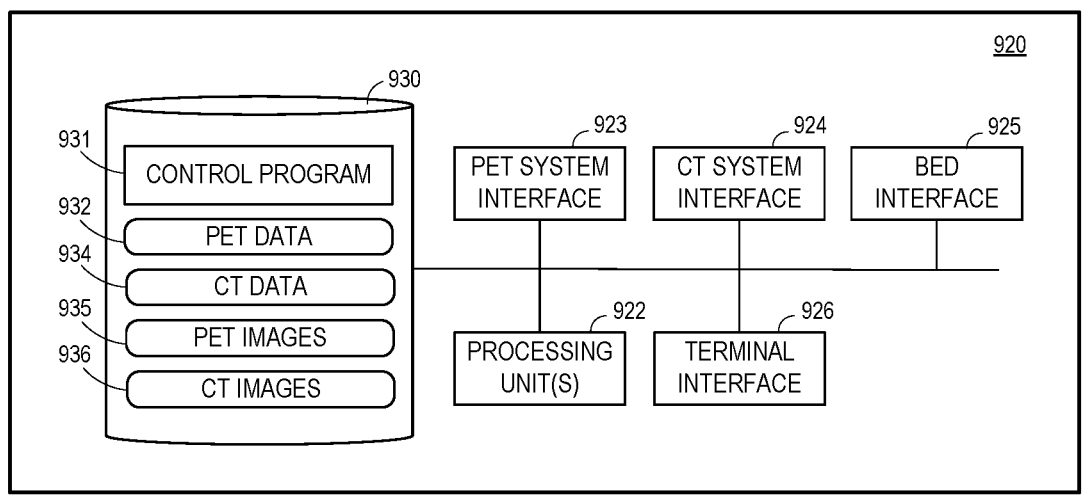
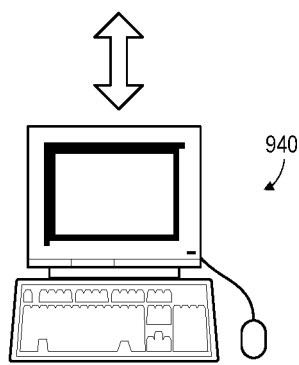
FIG. 9

SYSTEM FOR TIMING PICKOFF OF QUALIFIED SIGNALS

BACKGROUND

According to conventional positron-emission-tomography (PET) imaging, a radiopharmaceutical tracer is introduced into a patient body typically via arterial injection. Radioactive decay of the tracer generates positrons which eventually encounter electrons and are annihilated thereby. The annihilation event produces two photons which travel in approximately opposite directions.

A ring of detectors surrounding the body detects the photons, identifies "coincidences" based thereon, and reconstructs PET images based on the identified coincidences. A coincidence is identified when two detectors disposed on opposite sides of the body detect the arrival of two photons within a particular coincidence time window. Because the two "coincident" photons travel in approximately opposite directions, the locations of the two detectors determine a Line-of-Response (LOR) along which an annihilation event may have occurred. Time-of-flight (TOF) PET additionally measures the difference between the detection times of the two photons arising from the annihilation event. This difference may be used to more accurately estimate a particular position along the LOR at which the annihilation event occurred. Both coincidence detection and TOF measurements require extremely accurate and consistent determination of photon detection times.

Arrival of a photon at a detector causes the detector to generate an electrical signal, or pulse. Generally, a photon detection time is identified as a time (i.e., a "trigger" time) at which the generated pulse crosses a threshold voltage (i.e., a "trigger" voltage). A coincidence is identified if a trigger time of a pulse generated by one detector and a trigger time of a pulse generated by another detector are within the coincidence time window.

Not all pulses which cross the trigger voltage should be used to identify coincidences. For example, a pulse generated in response to reception of a scattered photon or other noise may cross the trigger voltage. In contrast, a valid pulse crosses the trigger voltage and also proceeds to voltage levels which are higher than those typically reached by a scatter- or noise-related pulse. Discriminator systems therefore attempt to discriminate valid pulses which should be used to identify coincidences from invalid pulses, which should not, by determining whether a pulse crosses an "arming" voltage which is greater than the trigger voltage.

A conventional leading edge discriminator (LED) includes analog elements (e.g., comparators) to determine whether an incoming signal has crossed the above-described trigger voltage and whether the signal has also crossed the arming voltage (i.e., is a valid pulse). An LED sets a first logic signal to high once the incoming signal has crossed the trigger voltage, and gates (e.g., using an AND gate or a D flip-flop) the first logic signal using a second logic signal which indicates whether the incoming signal has crossed the arming voltage. Generally, the first (high) logic signal is allowed to pass to a coincidence detection system once the second logic signal indicates that the incoming signal has crossed the arming voltage. In order to ensure that the second logic signal reaches the gate before the first logic signal in the case of a valid pulse, an LED includes an analog delay element prior to the gate to delay the first logic signal. The analog delay element adds jitter to the first logic signal due to electronics noise and process/voltage/temperature variations of its constituent components. The jitter affects the timing of the signal output by the gate, which is used to determine the trigger time of the valid pulse.

Conventional discriminators therefore introduce uncertainty and inaccuracy in all the trigger times determined by the system. This uncertainty and inaccuracy may result in mis-identified coincidences. Specifically, inaccurate trigger times will degrade coincidence time resolution and reduce event localization accuracy, thereby lowering system effective sensitivity. Systems are desired to increase the accuracy of trigger times determined for incoming valid pulses.

BRIEF DESCRIPTION OF THE DRAWINGS

FIGS. 1a and 1b illustrate detection of coincidence events according to some embodiments.

FIGS. 7a through 7f comprise tabular representations of data structures to record pulses and corresponding timings according to some embodiments.

FIG. 9 is a block diagram of a PET-CT imaging system according to some embodiments.

DETAILED DESCRIPTION

Figure 2:
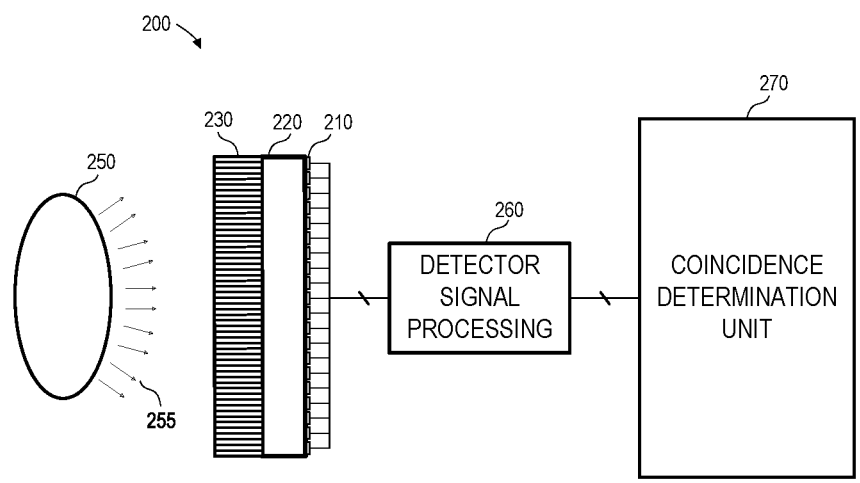
FIG. 2 is a block diagram of a coincidence determination system according to some embodiments.

The following description is provided to enable any person in the art to make and use the described embodiments. Various modifications, however, will remain apparent to those in the art.

Generally, some embodiments provide determination of pulse trigger times (i.e., timing pickoff) without using an analog delay element in a timing channel. Some embodiments use analog components to generate a first logic signal indicating whether a signal has crossed a trigger voltage and a second logic signal indicating whether the signal has crossed an arming voltage greater than the trigger voltage. Embodiments may further include digital components to determine, based on the logic signals, whether the signal is valid and a timing (i.e., a trigger time) of the signal. The digital components may be implemented using a Field-Programmable Gate Array (FPGA), a System on a Chip (SoC), a custom Application-Specific Integrated Circuit (ASIC) or other digital logic device.

Embodiments may therefore reduce analog circuit complexities and the effects of jitter on the determined trigger times. The digital components may also use reconfigurable logic to implement discrimination, which facilitates customization of the discrimination based on, for example, expected pulse shapes or expected time delays between the crossing of the trigger and arming thresholds.

Embodiments are also preferable to a purely digital implementation, which would require very high sampling rate analog-to-digital converters (ADCs), high-speed interfaces between ADCs and FPGAs, and high-end FPGAs. The power consumption and total cost of such an implementation will be significantly greater than that of some embodiments without providing significant, if any, improvement in timing pickoff performance.

FIG. 1a and FIG. 1B illustrate detection of coincidence events within a PET scanner according to some embodiments. FIG. 1a is an axial view of bore 105 of PET scanner detector ring 100 and imaging subject 110 disposed therein. Imaging subject 110 may comprise a human body, a phantom, or any other suitable subject. FIG. 1B is a transaxial view of detector ring 100 and body 110 of FIG. 1a. Detector ring 100 is composed of an arbitrary number (eight in this example) of adjacent and coaxial rings of detectors 150 in the illustrated example. Each detector 150 may comprise any number of scintillation elements and electrical transducers.

The scintillation elements create light photons with the energy of few electron volts (eV) in response to receiving the 511 keV gamma photons which result from annihilation events. Lutetium oxyorthosilicate (LSO) and other scintillators exhibit suitable stopping power and fast scintillation decay, and may be used in high count rate scenarios. The electrical transducers, or photosensors, convert the low-energy light photons created by the scintillation elements to electrical signals, sometimes referred to herein as pulses. According to some embodiments, the electrical transducers may comprise, for example, a scintillator combined with silicon photomultipliers (SiPMs), a scintillator combined with photomultiplier tubes (PMTs), or semiconductor-based detectors.

Annihilation events 120, 130, 140 and 142 are assumed to occur at various locations within subject 110. As described above, an injected tracer generates positrons which are annihilated by electrons to produce two 511 keV photons which travel in approximately opposite directions. Each of annihilation events 120, 130, 140 and 142 results in the detection of a coincidence. True coincidences represent valid image data, while scatter and random coincidences represent noise associated with incorrect event position information.

A coincidence is detected when a pair of detectors receive two annihilation photons within the coincidence time window. Event 120 is associated with a true coincidence because event 120 resulted in two photons which were detected within the coincidence time window and because the position of annihilation event 120 lies on LOR 125 connecting the detector positions at which the two photons were received.

Event 130 is associated with a scatter coincidence because, even though the two photons resulting from event 130 were detected within the coincidence time window, the position of annihilation event 130 does not lie on LOR 135 connecting the two photon positions. This may be due to Compton (i.e., inelastic) or Coherent (i.e., elastic) scatter resulting in a change of direction of at least one of the two annihilation photons within subject 110.

Events 140 and 142 are two separate annihilation events which result in detection of a random coincidence. In the present example, one of the photons generated by event 140 is absorbed in body 210 and one of the photons generated by event 142 escapes detection by any detector 150 of detector ring 100. The remaining photons happen to be detected within the coincidence time window, even though no annihilation event occurred on LOR 145 connecting the positions at which the coincident photons were received.

The detected events may be stored as raw (i.e., list-mode) data and/or sinograms. List-mode data may represent each annihilation event using data specifying a LOR and the time at which the event occurred. Since only the true unscattered coincidences indicate locations of annihilation events, random coincidences and scatter coincidences are often subtracted from or otherwise used to correct acquired list-mode data or sinograms during reconstruction of a PET image based thereon.

FIG. 2 illustrates PET detector ring portion 200 of a PET scanner according to some embodiments. Detector 200 includes detectors 210, optional light guide 220 and scintillator 230. Scintillator 230 may be pixelated (as shown), monolithic, or otherwise configured.

Detector ring portion 200 is positioned to detect gamma photons 255 emitted from volume 250. Systems for facilitating the emission of gamma photons from a volume are known in the art, and in particular with respect to the PET imaging described herein. As described above, scintillator 230 receives the gamma photons 255 and emits low-energy light photons in response. Detectors 210 receive the photons from scintillator 230 and each detector 210 generates electrical signals based on the energy of received photons and its own characteristic photoelectric response profile.

Embodiments are not limited to scintillator-based detectors. For example, direct conversion detectors (e.g., CZT and TlBr) which generate electrical signals based on received gamma photons may also be used in conjunction with some embodiments.

Detector signal processing unit 260 receives the electrical signals generated by each of detectors 210 and performs signal processing to determine trigger times of valid pulses and reject invalid pulses using a discriminator as described herein. Detector signal processing unit 260 may also, for example, perform signal unpiling by pile-up rejection and determine an event energy. Detector signal processing unit 260 may perform any suitable functions and exhibit any suitable implementations.

Coincidence determination unit 270 receives all valid pulses, called singles, detected by each detector of the detector ring and their corresponding trigger times as described herein. Coincidence determination unit 270 identifies a coincidence for each pair of pulses whose trigger times fall within a coincidence time window.

Figure 3:
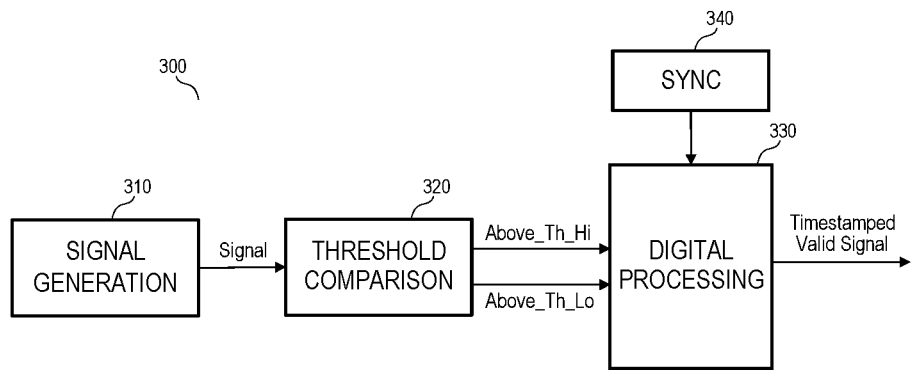
FIG. 3 is a block diagram of a timing pickoff system according to some embodiments.

FIG. 3 illustrates timing pickoff system 300 according to some embodiments. It should be noted that system 300 and the other implementations and processes described herein need not be limited to the processing of PET detector signals. Embodiments may be employed within any system requiring precise signal timing and noise rejection.

Signal generation component 310 generates analog signals. The analog signals may be initiated by the occurrence of any suitable event, such as the arrival of a light photon. In this regard, signal generation component 310 may comprise a PET detector including, for example, LSO scintillators coupled to a SiPM photosensor. Such a PET detector may generate and output a characteristic pulse in response to reception of a gamma photon as is known in the art.

Threshold comparison component 320 receives a signal from component 310 and evaluates the signal with respect to two programmable voltage thresholds. One threshold is denoted Th_Lo and may correspond to a trigger time threshold as described above, and the other, higher, threshold is denoted Th_Hi and may correspond to an arming threshold. According to FIG. 3, logic signal Above_Th_Lo is held high by threshold comparison component 320 while the voltage of the signal received from signal generation component 310 is greater than Th_Lo (and low while it is not). Similarly, logic signal Above_Th_Hi is held high by threshold comparison component 320 while the voltage of the signal received from signal generation component 310 is greater than Th_Hi (and low while it is not).

Threshold comparison component 320 comprises an analog circuit and does not include an analog delay component which adds jitter to either of its output signals. Embodiments are not limited to the above-described output signals of threshold comparison component 320. Generally, threshold comparison component 320 may output two logic signals from which digital processing component 330 can determine whether the voltage of a signal received from signal generation component 310 is below Th_Lo, between Th_Lo and Th_Hi, or above Th_Hi.

Digital processing component 330 may comprise an FPGA, an SoC or any other suitable device. Digital processing component 330 performs discrimination and timing pickoff of a pulse output by signal generation component 310 based on the output logic signals of threshold comparison component 320.

The timing (i.e., trigger time) of an incoming pulse may be equal to the time at which the pulse voltage exceeds Th_Lo. As described, crossing Th_Lo causes transition of logic signal Above_Th_Lo to a high state, which may in turn trigger digital processing component 330 to read the value of a timing measurement unit (e.g., a counter) running within digital processing component 330. The value of the timing measurement unit represents the trigger time of the pulse received by threshold comparison component 320. Sync component 340 periodically transmits a sync signal to digital processing component 330 to synchronize the trigger time of each detector which references to the timing measurement unit.

Digital processing component 330 may then determine that the received pulse is valid only if the pulse voltage exceeds Th_Hi (i.e., logic Above_Th_Hi transitions to a high state) within a given time period after the pulse voltage exceeded Th_Lo. The valid pulse is timestamped with the read counter value.

In the case of a PET scanner implementation, the trigger time is the time at which a photon created by an annihilation event is considered to have reached signal generation component 310 (i.e., a PET detector). This trigger time may be used to identify coincidences with other pulses generated by other PET detectors of the PET scanner which are validated as described above and timestamped using common sync component 340. That is, the counters used to determine the timing of pulses received from each PET detector are referenced simultaneously by a common sync signal, such that differences in timing measurement unit values accurately represent differences in trigger times.

Figure 4:
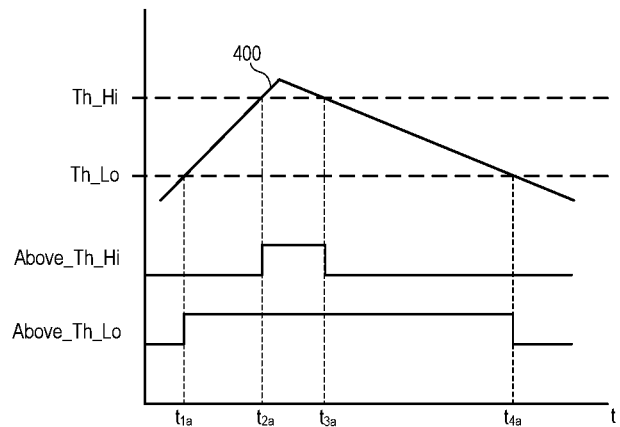
FIG. 4 illustrates an incoming signal and corresponding signals generated by a timing pickoff system over time according to some embodiments.

FIG. 4 illustrates pulse 400 output by a detector according to some embodiments. The shape of pulse 400 is approximated and does not represent a typical detector response, which exhibits a higher-order function.

Voltage Th_Lo represents a trigger voltage as described above. The time at which pulse 400 crosses trigger voltage Th_Lo defines trigger time $t_{1a}$ which is associated with the event which caused signal 400. As shown in FIG. 4, logic signal Above_Th_Lo output by comparators 320 goes high at time $t_{1a}$ and remains so until pulse 400 dips below trigger voltage Th_Lo at time $t_{4a}$. Logic signal Above_Th_Hi goes high at time $t_{2a}$ in response to crossing of arming voltage Th_Hi and stays high until the voltage of pulse 400 drops below arming voltage Th_Hi at time $t_{4a}$.

According to some embodiments, digital processing component 300 detects the transition of logic signal Above_Th_Lo at time $t_{1a}$ and, in response, waits to see whether logic signal Above_Th_Hi goes high within a predefined time period after time $t_{1a}$. Assuming that time $t_{2a}$ is within the predefined time period, digital processing component 300 detects the transition of logic signal Above_Th_Lo at time $t_{2a}$ and, in response, determines that pulse 400 is valid and assigns trigger time $t_{1a}$ to pulse 400.

Digital processing component 330 may identify a situation in which logic signal Above_Th_Lo goes high and then goes low within the predefined time period before logic signal Above_Th_Hi goes high. Such a situation may allow digital processing component 330 to identify an invalid pulse without waiting for the entire predefined time period.

Figure 5:
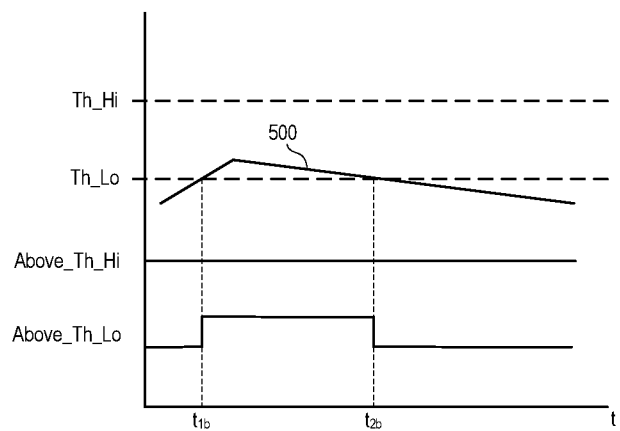
FIG. 5 illustrates an incoming signal and corresponding signals generated by a timing pickoff system over time according to some embodiments.

FIG. 5 illustrates pulse 500 output by a detector according to some embodiments. The voltage of pulse 500 crosses Th_Lo at time $t_{1b}$ and logic signal Above_Th_Lo output by comparators 320 goes high at that time in response. The voltage of pulse 500 then drops below Th_Lo at time $t_{2b}$ without ever crossing Th_Hi. Logic signal Above_Th_Lo goes low at time $t_{2b}$. If time $t_{2b}$ is within the predefined time period from time $t_{1b}$, digital processing component 330 may determine that pulse 500 is invalid at $t_{2b}$ without waiting for the remainder of the predefined time period. If $t_{2b}$ is not within the predefined time period from time $t_{1b}$, digital processing component 330 may determine that pulse 500 is invalid at the expiration of the predefined time period, because logic signal Above_Th_Hi did not go high during the predefined time period.

Figure 6:
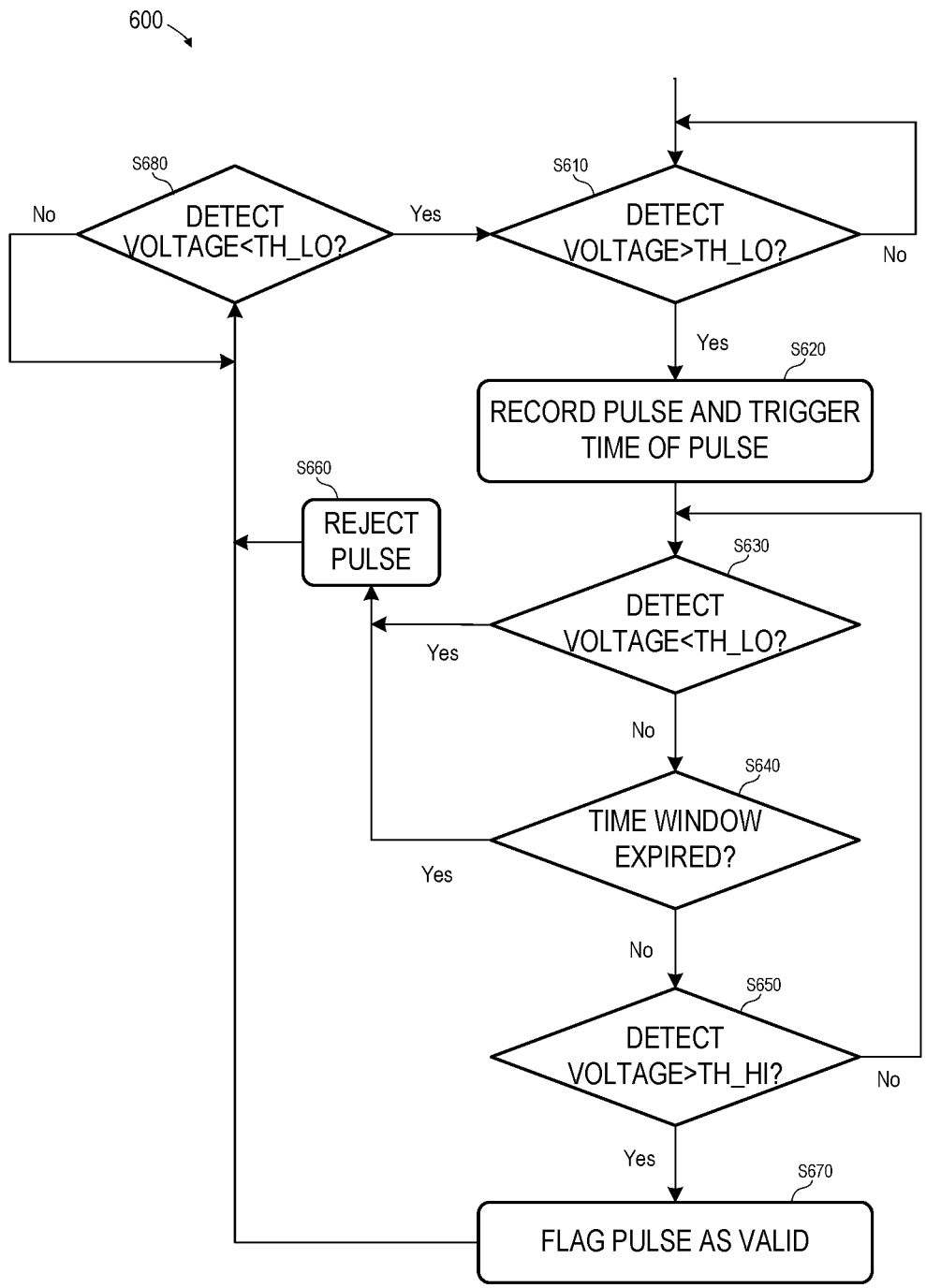
FIG. 6 is a flow diagram of a process to determine the timing of valid pulses according to some embodiments.

FIG. 6 is a flow diagram of process 600 to determine the timing of valid pulses according to some embodiments. Process 600 may therefore by executed to determine whether an incoming pulse is valid and to determine a timing to associate with the incoming pulse. As described above, validity may indicate that the pulse represents a PET singles event and the timing may represent a trigger time which is used to identify a coincidence with another valid pulse. Process 600 may be performed by a digital processing component such as digital processing component 330 of FIG. 3. It should be noted that embodiments may comprise any other logic and criteria for discriminating valid pulses and determining associated timings.

Initially, flow cycles at S610 until it is determined that a voltage of an incoming pulse has exceeded a voltage Th_Lo. S610 may therefore comprise monitoring a logic signal (e.g., Above_Th_Lo) which is low in a case that the voltage of the incoming pulse is below Th_Lo and is high in a case that the voltage of the incoming pulse is above Th_Lo. The voltage Th_Lo may be any predefined voltage suitable to the particular system in which process 600 is implemented. In some embodiments, voltage Th_Lo is intended to detect the point of a leading edge of a PET detector-generated pulse from which a trigger time of the pulse is determined.

According to some embodiments, the logic signal monitored at S610 is generated by analog-to-logic components which do not include an analog delay element. Absence of such an analog delay element reduces jitter and noise exhibited by the logic signal. Since the timing of the incoming pulse is determined based on the time at which the logic signal indicates that the pulse exceeds a voltage Th_Lo, absence of an analog delay element results in increased timing accuracy for the pulse.

Flow proceeds from S610 to S620 once it is determined that the voltage of the incoming pulse has exceeded the voltage Th_Lo. At S620, a record is created identifying the pulse and the trigger time of the pulse. The trigger time may comprise a value read from a timing measurement unit in response to an affirmative determination at S610.

The record may be created at S620 within any suitable data structure stored in any suitable memory device or devices. FIG. 7a illustrates table 700 associated with a particular PET detector (i.e., detector d2390) of a PET scanner. Table 700 is used to identify valid pulses generated by the particular PET detector and their corresponding trigger times. Embodiments are not limited to the structure of table 700.

FIG. 7a illustrates population of trigger time ti within a record represented an incoming pulse at S620. Next, flow cycles between S630, S640 and S650 until it is determined at S630 that the voltage of the incoming pulse has dropped below Th_Lo, until it is determined at S640 that a time window from ti has expired, or until it is determined at S650 that the voltage of the incoming pulse is greater than Th_Hi. Although the determinations at S630, S640 and S650 are illustrated sequentially, it should be understood that the determinations may occur substantially simultaneously, in that each condition is monitored in response to the detection at S610.

It will be assumed in the present example that it is determined at S630 that the voltage of the incoming pulse has dropped below Th_Lo. Since the voltage dropped below Th_Lo prior to exceeding Th_Hi, it is assumed that the pulse is an invalid pulse. Flow therefore proceeds to S660 to reject the pulse. FIG. 7b illustrates updating table 700 at S660 to reject the pulse. Flow continues to S680 at which it is determined that the voltage is below Th_Lo, and then returns to S610 to detect another leading edge.

It will now be assumed that a voltage exceeding Th_Lo (i.e., a leading edge) is again detected at S610 and a corresponding record of table 700 is created as shown in FIG. 7c. At S640, it is determined that a time window from the current ti (i.e., 39) has expired. The time window may be defined as a maximum time which could be expected to elapse, in the case of a valid pulse, between the crossing of Th_Lo to the crossing of Th_Hi. Flow therefore proceeds to S660 to reject the pulse, continues to S680 to pause until the voltage drops below Th_Lo, and then returns to S610 to detect another leading edge. FIG. 7d illustrates updating table 700 at S660 to reject the pulse associated with time ti.

A voltage exceeding Th_Lo is once again detected at S610 and a corresponding record of table 700 is created as shown in FIG. 7e. At S650, it is determined that the voltage exceeds Th_Hi. S650 may comprise monitoring a logic signal (e.g., Above_Th_Hi) which is low in a case that the voltage of the incoming pulse is below Th_Hi and is high in a case that the voltage of the incoming pulse is above Th_Hi. Th_Hi may be set to a predefined value which, in conjunction with the predetermined time window, form criteria intended to discriminate valid pulses from invalid pulses.

Flow therefore proceeds to S670 after a positive determination at S660. At S670, the pulse is flagged as valid, for example as shown in FIG. 7f. Flow then continues to S680 and proceeds as described above.

Table 700 therefore tracks valid pulses generated by detector d2390 during an image acquisition and their respective timings in the digital domain. As is known in the art, these timings may be used to determine coincidences with valid pulses generated by other detectors of the PET scanner. As is also known in the art, other information such as pulse energy, pulse shape and the like may be determined for each incoming valid pulse and used during PET image processing.

Figure 8:
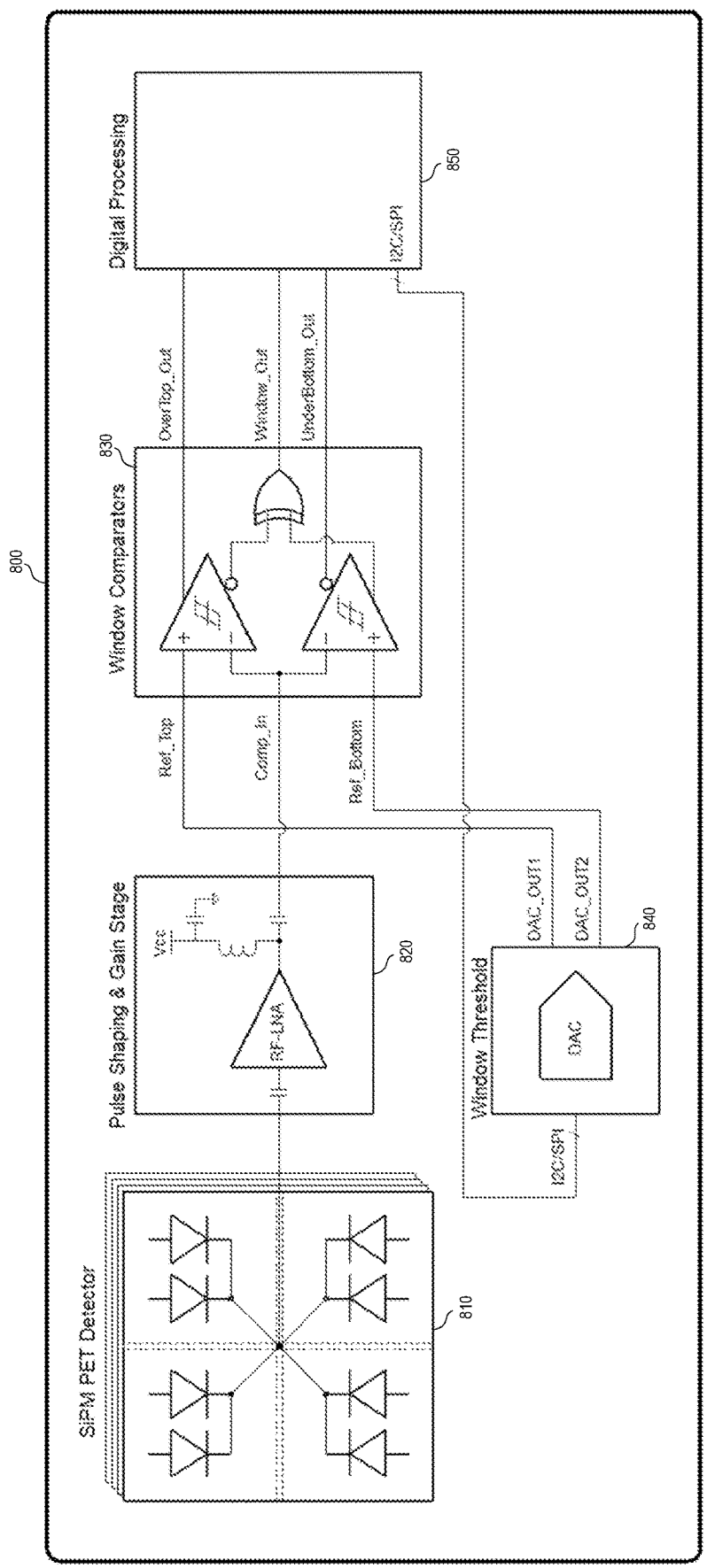
FIG. 8 is a block diagram of a timing pickoff system according to some embodiments.

FIG. 8 is a block diagram of timing pickoff hardware system 800 according to some embodiments. System 800 may comprise an implementation of system 300 described above, but embodiments are not limited thereto. System 800 includes PET detector 810 for generating pulses as described herein. Pulse shaping and gain stage 820 amplifies and shapes a generated pulse as is known in the art prior to passing the shaped and amplified pulse to window comparators 830 as analog signal Comp_In.

Window comparators 830 may comprise an implementation of threshold comparison component 320 of system 300. Window comparators 830 comprise analog components and generate three logic signals based on voltage thresholds Ref_Bottom (e.g., trigger voltage, Th_Lo) and Ref_Top (e.g., arming voltage, Th_Hi). Logic signal Window_Out is high if the voltage of signal Comp_In is between Ref_Bottom and Ref_Top, logic signal UnderBottom_Out is high if the voltage of signal Comp_In is less than Ref_Bottom, and logic signal OverTop_Out is high if the voltage of signal Comp_In is greater than Ref_Top.

Both of logic signals Window_Out and UnderBottom_Out change state when signal Comp_In exceeds Ref_Bottom, and the trigger time of Comp_In may therefore be determined from either logic signal. Advantageously, system 800 includes no analog delay element in the signal chain from PET detector 810 to either of logic signals Window_Out and UnderBottom_Out. Accordingly, system 800 does not contribute jitter and/or noise which would be associated with such an analog delay element to these logic signals.

According to system 800, the values of voltages Ref_Bottom and Ref_Top are set by window threshold component 840. Window threshold component 840 may comprise a digital to analog converter (DAC) which receives digital control signals from digital processing component 850 specifying the voltage values to which Ref_Bottom and Ref_Top should be respectively set. Window threshold component 840 outputs analog signals Ref_Bottom and Ref_Top exhibiting the specified voltages from its outputs DAC_OUT1 and DAC_OUT2 to window comparators 830. Advantageously, digital processing component 850 may therefore control the values of Ref_Bottom and Ref_Top on a system-wide or detector-specific basis in view of system characteristics and calibration activities to ensure consistency in determination of trigger times with respect to each detector of the PET scanner. Embodiments are not limited to generation of Ref_Bottom and Ref_Top based on signals received from digital processing component 850.

Digital processing component 850 may comprise an implementation of digital processing component 330 of system 300. Accordingly, digital processing component may comprise an FPGA, a SoC or other device and may operate to perform process 600. Digital processing component 850 may use logic other than that described herein to discriminate valid signals and determine trigger times thereof. Such logic may be based on any two of signals OverTop_Out, Window_Out, and UnderBottom_Out, or on all three signals.

FIG. 9 illustrates PET/CT imaging system 900 to execute one or more of the processes described herein. Embodiments are not limited to system 900, to a multi-modality imaging system, or to an imaging system.

System 900 includes gantry 910 defining bore 912. As is known in the art, gantry 910 houses PET imaging components for acquiring PET image data and CT imaging components for acquiring CT image data. The CT imaging components may include one or more x-ray tubes and one or more corresponding x-ray detectors as is known in the art. The PET imaging components may include any number or type of detectors in any configuration as is known in the art. Pulses generated by such detectors may be processed by analog and digital components as described herein to discriminate valid pulses and determine trigger times for the valid pulses.

Bed 915 and base 916 are operable to move a patient lying on bed 915 into and out of bore 912 before, during and after imaging. In some embodiments, bed 915 is configured to translate over base 916 and, in other embodiments, base 916 is movable along with or alternatively from bed 915.

Movement of a patient into and out of bore 912 may allow scanning of the patient using the CT imaging elements and the PET imaging elements of gantry 910. Bed 915 and base 916 may provide continuous bed motion and/or step-and-shoot motion during such scanning according to some embodiments.

Control system 920 may comprise any general-purpose or dedicated computing system. Accordingly, control system 920 includes one or more processing units 922 configured to execute processor-executable program code to cause system 920 to acquire image data and generate images therefrom, and storage device 930 for storing the program code. Storage device 930 may comprise one or more fixed disks, solid-state random-access memory, and/or removable media (e.g., a thumb drive) mounted in a corresponding interface (e.g., a Universal Serial Bus port).

Storage device 930 stores program code of control program 931. One or more processing units 922 may execute control program 931 to, in conjunction with PET system interface 923 and bed interface 925, control hardware elements to inject a radiopharmaceutical into a patient, move the patient into bore 912 past PET detectors of gantry 910, and detect coincidences occurring within the patient based on pulses generated by the PET detectors. The detected events may be stored in storage 930 as PET data 932, which may comprise raw (i.e., list-mode) data and/or sinograms. Control program 931 may also be executed to reconstruct PET images 935 based on PET data 932 using any suitable reconstruction algorithm that is or becomes known.

One or more processing units 922 may execute control program 931 to control CT imaging elements of system 900 using CT system interface 924 and bed interface 925 to acquire CT data 934. Any suitable reconstruction algorithm may be utilized to generate CT images 936 based on CT data 934. According to some embodiments, PET images 935 may be generated based at least in part on CT data 934 (e.g., using a linear attenuation coefficient map determined from CT data 934).

PET images 935 and CT images 936 may be transmitted to terminal 940 via terminal interface 926. Terminal 940 may comprise a display device and an input device coupled to system 920. Terminal 940 may display the received PET images 935 and CT images 936. Terminal 940 may receive user input for controlling display of the data, operation of system 900, and/or the processing described herein. In some embodiments, terminal 940 is a separate computing device such as, but not limited to, a desktop computer, a laptop computer, a tablet computer, and a smartphone.

Each component of system 900 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Those in the art will appreciate that various adaptations and modifications of the above-described embodiments can be configured without departing from the claims. Therefore, it is to be understood that the claims may be practiced other than as specifically described herein.

What is claimed is:

1. A positron emission tomography scanner system comprising:
    a plurality of detectors to output electrical pulses;
    an analog circuit to receive a first pulse from a first one of the plurality of detectors and to output a first logic signal indicating whether or not a voltage of the first pulse is greater than a first threshold voltage and to output a second logic signal indicating whether or not the voltage of the first pulse is greater than a second threshold voltage; and
    a digital processing component to receive the first logic pulse and the second logic pulse and to determine, based on the second logic signal, if the first pulse is valid and to determine, based on the first logic signal, a first trigger time associated with the first pulse.

2. A system according to claim 1, wherein the analog circuit does not comprise an analog delay element.

3. A system according to claim 1, further comprising a threshold component to receive one or more logic signals from the digital processing component specifying the first threshold voltage and the second threshold voltage, and to output a first analog signal having the first threshold voltage and a second analog signal having the second threshold voltage.

4. A system according to claim 1, further comprising:
    a second analog circuit to receive a second pulse from a second one of the plurality of detectors and to output a third logic signal indicating whether or not a voltage of the second pulse is greater than the first threshold voltage and to output a fourth logic signal indicating whether or not the voltage of the second pulse is greater than the second threshold voltage,
    wherein the digital processing component is to receive the third logic signal and the fourth logic signal and to determine, based on the fourth logic signal, if the second pulse is valid and to determine, based on the third logic signal, a second trigger time associated with the second pulse.

5. A system according to claim 4, further comprising:
    a sync component to provide a sync signal to the digital processing component, where the digital processing component determines the first trigger time and the second trigger time based on the sync signal and a timing measurement unit of the digital processing component; and
    a coincidence determination unit to identify, based on the first trigger time and the second trigger time, a coincidence including the first pulse and the second pulse.

6. A system according to claim 4, wherein the analog circuit does not comprise an analog delay element, and
    wherein the second analog circuit does not comprise an analog delay element.

7. A system according to claim 1, further comprising:
    a sync component to provide a sync signal to the digital processing component, where the digital processing component determines the first trigger time based on the sync signal and a timing measurement unit of the digital processing component.

8. A method comprising:
receiving a first analog signal;
outputting a first logic signal indicating whether or not a voltage of the first analog signal is greater than a first threshold voltage;
outputting a second logic signal indicating whether or not the voltage of the first analog signal is greater than a second threshold voltage;
determining, based on the second logic signal, if the first analog signal is valid; and
determining, based on the first logic signal, a first trigger time associated with the first analog signal.

9. A method according to claim 8, wherein none of receiving the first analog signal, outputting the first logic signal, and determining the first trigger time comprise operating an analog delay element.

10. A method according to claim 8, further comprising:
receiving one or more logic signals specifying the first threshold voltage and the second threshold voltage; and
outputting a second analog signal having the first threshold voltage and a third analog signal having the second threshold voltage.

11. A method according to claim 8, further comprising:
receive a second analog signal;
outputting a third logic signal indicating whether or not a voltage of the second analog signal is greater than the first threshold voltage;
outputting a fourth logic signal indicating whether or not the voltage of the second analog signal is greater than the second threshold voltage;
determining, based on the fourth logic signal, if the second analog signal is valid; and
determining, based on the third logic signal, a second trigger time associated with the second analog signal.

12. A method according to claim 11, further comprising:
receiving a sync signal, where the first trigger time and the second trigger time are determined based on the sync signal and on a timing measurement unit reset by the sync signal; and
identifying, based on the first trigger time and the second trigger time, a coincidence including the first analog signal and the second analog signal.

13. A method according to claim 11, wherein none of receiving the first analog signal, outputting the first logic signal, determining the first trigger time, receiving the second analog signal, outputting the third logic signal, and determining the second trigger time comprise operating an analog delay element.

14. A system comprising:
an analog circuit to:
receive a first electrical signal;
output a first logic signal indicating whether or not a voltage of the first pulse is greater than a first threshold voltage; and
output a second logic signal indicating whether or not the voltage of the first pulse is greater than a second threshold voltage; and
a digital processing component to:
receive the first logic signal and the second logic signal;
determine, based on the second logic signal, if the first pulse is valid; and
determine, based on the first logic signal, a first trigger time associated with the first pulse.

15. A system according to claim 14, wherein the analog circuit does not comprise an analog delay element.

16. A system according to claim 15, further comprising:
a sync component to provide a sync signal to the digital processing component, where the digital processing component determines the first trigger time based on the sync signal and a timing measurement unit of the digital processing component, wherein the timing measurement unit is reset by the sync signal.

17. A system according to claim 14, further comprising a threshold component to receive one or more logic signals from the digital processing component specifying the first threshold voltage and the second threshold voltage, and to output a first analog signal having the first threshold voltage and a second analog signal having the second threshold voltage.

18. A system according to claim 14, further comprising:
a second analog circuit to:
receive a second electrical signal;
output a third logic signal indicating whether or not a voltage of the second electrical signal is greater than the first threshold voltage; and
output a fourth logic signal indicating whether or not the voltage of the second electrical signal is greater than the second threshold voltage,
wherein the digital processing component is to:
receive the third logic signal and the fourth logic signal;
determine, based on the fourth logic signal, if the second electrical signal is valid; and
determine, based on the third logic signal, a second trigger time associated with the second electrical signal.

19. A system according to claim 18, further comprising:
a sync component to provide a sync signal to the digital processing component, where the digital processing component determines the first trigger time and the second trigger time based on the sync signal and a timing measurement unit of the digital processing component, wherein the timing measurement unit is reset by the sync signal.

20. A system according to claim 18, wherein the analog circuit does not comprise an analog delay element, and
wherein the second analog circuit does not comprise an analog delay element.

* * * * *